United States Patent [19]

van der Puy

[11] Patent Number: 5,081,275
[45] Date of Patent: Jan. 14, 1992

[54] PROCESS FOR THE PREPARATION OF 2-FLUOROBENZONITRILE FROM SACCHARIN

[75] Inventor: Michael van der Puy, Cheektowaga, N.Y.

[73] Assignee: Allied-Signal Inc., Morristown, N.J.

[21] Appl. No.: 543,234

[22] Filed: Jun. 25, 1990

[51] Int. Cl.$^5$ .............. C07C 253/20; C07C 253/00; C07C 253/30
[52] U.S. Cl. .................................. 558/425; 558/310
[58] Field of Search ........................... 558/425, 310

[56] References Cited

U.S. PATENT DOCUMENTS 4,124,631 11/1978 Hayami et al. .................. 260/465.6
4,886,629 12/1989 van der Puy .................... 562/826

OTHER PUBLICATIONS

CA 89:179720x-(1978), vol. 89, Hayami et al.
CA 71:80992d (1969), Badiache Anilin-vol. 71.
CA 99:87839W (1983), Ishihard et al., vol. 99.
CA 105:114707c (1986), Ishikowa et al., vol. 105.
CA 109:92451t (1988), Ishikawa et al., vol. 101.
"O-Cyanobenzenesulphonic Acid and Its Derivatives", by A. J. Walker et al., J. Chem. Soc., 89 (1906), pp. 350-353.
"Phase Transfer Catalysis, Preparation of Aliphatic and Aromatic Sulfonyl Fluorides" by T. Bianchi et al., J. Org. Chem. 42 (1977) pp. 2031-2032.
"Potassium Fluoride Catalyzed Fluorodesulfonylations of Aryl Sulfonyl Fluorides" by M. Van Der Puy, J. of Org. Chem. (1988), 53, pp. 4399-4401.
"Benzenesulphonyl Fluoride Derivatives" by W. Davies et al., (1932), J. Chem. Soc., pp. 2042-2046.
"Tetraphenylphosphonium Bromide Catalyzed Fluorodenitrations and Fluorodesulfonylations" by N. Yazawa et al., Chemistry Letter, 1989, pp. 2213-2216.
"Aromatic Sulphonyl Fluorides" by W. Davies et al., J. Chem. Soc., (1932), pp. 2104-2109.
"Preparation of Aroyl and Arenesulfonyl Fluorides . . . ", pp. 1267-1268, by A. Sekiya et al., Bull. Chem. Soc. of Japan, (1978), 51.
"Sulfonyl Fluorides as Inhibitors of Esterases . . . " by D. Fahrney et al., J. Am. Chem. Soc., 85, (1963), p. 997.

Primary Examiner—Joseph Paul Brust
Attorney, Agent, or Firm—Melanie L. Brown; Jay P. Friedenson

[57] ABSTRACT

The present invention relates to a process for the preparation of 2-fluorobenzonitrile. The process comprises the steps of:

(a) heating saccharin and phosphorus pentachloride under conditions and for a time sufficient to provide 2-cyanobenzenesulfonyl chloride; and (b) reacting the 2-cyanobenzenesulfonyl chloride with alkali metal fluoride in solvent for said 2-cyanobenzenesulfonyl chloride under conditions and for a time sufficient to provide 2-fluorobenzonitrile.

The present invention provides a process for the preparation of 2-fluorobenzonitrile which is a versatile intermediate for a variety of 2-fluoro substituted benzenes. For example, hydrolysis of 2-fluorobenzonitrile leads to 2-fluorobenzoic acid or 2-fluorobenzamide while reduction of 2-fluorobenzonitrile leads to 2-fluorobenzylamine. Also, the reaction of 2-fluorobenzonitrile with organometallic reagents results in various 2-fluorophenyl ketones.

20 Claims, No Drawings

5,081,275

PROCESS FOR THE PREPARATION OF 2-FLUOROBENZONITRILE FROM SACCHARIN

FIELD OF THE INVENTION

This invention relates to a process for the preparation of 2-fluorobenzonitrile.

BACKGROUND OF THE INVENTION

A versatile intermediate for a variety of 2-fluoro substituted benzenes is 2-fluorobenzonitrile. For example, hydrolysis of 2-fluorobenzonitrile leads to 2-fluorobenzoic acid or 2-fluorobenzamide while reduction of 2-fluorobenzonitrile leads to 2-fluorobenzylamine. Also, the reaction of 2-fluorobenzonitrile with organometallic reagents results in various 2-fluorophenyl ketones.

Most processes for the preparation of 2-fluorobenzonitrile fall into one of two categories. In the first type, a 2-fluoro substituted benzene derivative is transformed into the cyano compound by way of a functional group interconversion. For example, U.S. Pat. No. 4,124,631 teaches that 2-fluorotoluene would be converted by ammoxidation into 2-fluorobenzonitrile; disadvantages of this method are that a reaction temperature of 300° to 650° C. is required and 2-fluorotoluene is an expensive starting material. As another example, CA 71:80992d(1969) teaches that 2-fluorobenzoic acid would react with a nitrile to form 2-fluorobenzonitrile; one disadvantage of this method is that 2-fluorobenzoic acid is an expensive starting material.

In the other type, 2-chlorobenzonitrile is converted with potassium fluoride to 2-fluorobenzonitrile in a variety of solvents and with or without additives such as phase transfer catalysts. One disadvantage of this method is that 2-chlorobenzonitrile is an expensive starting material. CA 99:87839w(1983) teaches that 2-chlorobenzonitrile is converted with potassium fluoride in 1,3-dimethyl-2-imidazolidinone to 2-fluorobenzonitrile. CA 105:114707c(1986) teaches that 2-chlorobenzonitrile is mixed with potassium fluoride in tetramethylene sulfone and refluxed for 30 hours to form 2-fluorobenzonitrile; this method is particularly disadvantageous because the reaction time is so long. CA 109:92451t(1988) teaches refluxing 2-chlorobenzonitrile and potassium fluoride in sulfolane in the presence of meta-$C_6H_4(NO_2)_2$ for 24 hours to give 2-fluorobenzonitrile.

N. Yazawa et al., "Tetraphenylphosphonium Bromide Catalyzed Fluorodenitrations and Fluorodesulfonylations. Efficient Syntheses of m-Fluoroaromatic Compounds," CHEMISTRY LETTERS. 2213 (1989) teaches the reaction of 3-nitrobenzonitrile with tetraphenylphosphonium bromide and phthaloyl chloride to form 3-fluorobenzonitrile.

It is desired to have a process for the preparation of 2-fluorobenzonitrile wherein the starting material is inexpensive.

SUMMARY OF THE INVENTION

The present invention provides a process for the preparation of 2-fluorobenzonitrile. The process comprises the step of:

heating 2-cyanobenzenesulfonyl chloride with alkali metal fluoride in solvent for the 2-cyanobenzenesulfonyl chloride to a temperature of about 170° C. to about 250° C. for a time sufficient to provide 2-fluorobenzonitrile.

The present invention also provides a process comprising the steps of:

(a) heating saccharin and phosphorus pentachloride under conditions and for a time sufficient to provide 2-cyanobenzenesulfonyl chloride; and (b) reacting said 2-cyanobenzenesulfonyl chloride with alkali metal fluoride in solvent for said 2-cyanobenzenesulfonyl chloride under conditions and for a time sufficient to provide 2-fluorobenzonitrile.

Other objects and advantages of the invention will become apparent from the following description.

DETAILED DESCRIPTION OF THE INVENTION

In one embodiment of the present invention, 2-cyanobenzenesulfonyl chloride is heated with alkali metal fluoride in a solvent for the 2-cyanobenzenesulfonyl chloride at a temperature of about 170° C. to about 250° C. for a time sufficient to provide 2-fluorobenzonitrile.

To prepare 2-cyanobenzenesulfonyl chloride, saccharin is used as the starting material. It should be understood that the term "saccharin" as used herein includes the sodium salt of saccharin. The use of saccharin as a starting material is advantageous because saccharin is inexpensive and available in commercial quantities.

Saccharin and phosphorus pentachloride are heated under conditions and for a time sufficient to provide 2-cyanobenzenesulfonyl chloride. The product may also contain pseudosaccharin chloride. This reaction is known as taught by A. J. Walker et al., "XXXIX—O-Cyanobenzenesulphonic Acid and its Derivatives", J. Chem. Soc. 89, 350 (1906) and W. Davies et al., "285. Benzenesulphonyl Fluoride Derivatives", J. Chem. Soc. 2042 (1932).

Commercially available saccharin, the sodium salt of saccharin, and phosphorus pentachloride may be used in the present invention. The molar ratio of saccharin to phosphorus pentachloride is preferably about 0.3:1 to about 1:1, more preferably about 0.4:1 to about 0.7:1, and most preferably about 0.4:1 to about 0.6:1.

The saccharin and phosphorus pentachloride are heated to a temperature sufficient to initiate the reaction; evidence of reaction initiation is the evolution of hydrogen chloride. The temperature is preferably about 50° C. to about 150° C., more preferably about 60° C. to about 120° C., and most preferably about 60° C. to about 90° C.; operation at this low temperature range is most preferred because it minimizes the formation of pseudosaccharin chloride. The time required for reaction depends upon the temperature used. Typically, the reaction time for converting saccharin to 2-cyanobenzenesulfonyl chloride is about one to about three hours.

When the evolution of hydrogen chloride ceases, the product, which may be a mixture of 2-cyanobenzenesulfonyl chloride and pseudosaccharin chloride, is isolated by pouring the cooled reaction mixture into water and filtering the product.

Unlike the teachings of W. Davies et al., Id., wherein 2-cyanobenzenesulfonyl chloride is separated from any pseudosaccharin chloride in the Product prior to further reaction, the present inventor has found that such separation is unnecessary in the present invention. The mixture of 2-cyanobenzenesulfonyl chloride and pseudosaccharin chloride is reacted with alkali metal fluoride in solvent for the 2-cyanobenzenesulfonyl chloride under conditions and for a time sufficient to provide 2-fluorobenzonitrile. In one embodiment, the mixture is heated to a temperature of about 170° C. to about 250° C. Preferably, the mixture is heated with stirring to a temperature of about 210° C. to about 245° C. and more preferably, about 225° C. to about 235° C.

The alkali metal fluoride is an alkali metal fluoride selected from the group consisting of sodium fluoride, potassium fluoride, rubidium fluoride, and cesium fluoride. Commercially available sodium fluoride, potassium fluoride, rubidium fluoride, and cesium fluoride may be used in the present invention. The preferred alkali metal fluoride is potassium fluoride which has been spray-dried so as to provide finely divided particles.

The molar ratio of the mixture of 2-cyanobenzenesulfonyl chloride and pseudosaccharin chloride to the alkali metal fluoride is preferably about 1:1.1 to about 1:8. More preferably, the molar ratio is about 1:3 to about 1:6, and most preferably, the molar ratio is about 1:4 to about 1:5.

The 2-cyanobenzenesulfonyl chloride is reacted with alkali metal fluoride in solvent for the 2-cyanobenzenesulfonyl chloride. Any inert polar organic solvent may be used. Preferred solvents are amide solvents such as dimethylformamide, N-methylpyrrolidinone, sulfoxide solvents such as dimethylsulfoxide, and sulfone solvents. Most of these solvents are available in commercial quantities. Sulfone solvents are more preferred because they are most inert under the operating conditions of the present process.

Of the sulfone solvents, the most preferred are aliphatic sulfones of the formula: $R_1—SO_2—R_2$ where $R_1$ and $R_2$ are the same or different and are alkyl groups of generally about 1 to about 8 carbon atoms, and preferably, about 1 to about 4 carbon atoms or $R_1$ and $R_2$ together are alkylene units of about 4 to about 5 carbon atoms. Illustrative aliphatic sulfone solvents include dimethylsulfone, diethylsulfone, dipropylsulfone, dibutylsulfone, dipentylsulfone, dihexylsulfone, diheptylsulfone, dioctylsulfone, methylethylsulfone, tetramethylenesulfone, and pentamethylenesulfone. The most preferred aliphatic sulfone solvent is tetramethylenesulfone. Most of the aliphatic sulfone solvents are available in commercial quantities; otherwise, the compounds may be prepared by oxidation of the appropriate alkyl sulfide.

The purpose of the solvent is to dissolve the 2-cyanobenzenesulfonyl chloride and any pseudosaccharin chloride present so as to form a stirrable mixture. Thus, as those skilled in the art will appreciate, the amount of solvent needed will depend upon the particular solvent selected.

The time required for reaction depends upon the temperature used. Typically, the reaction time for converting the 2-cyanobenzenesulfonyl chloride to 2-fluorobenzonitrile is about one to about four hours.

The 2-fluorobenzonitrile is isolated from the reaction mixture by using a known technique such as distillation. The preferred isolation technique is distillation because it permits the solvent to be recycled without any need for additional purification.

The preceding embodiment is advantageous because 2-cyanobenzenesulfonyl chloride, which can be prepared from inexpensive saccharin, is converted to 2-fluorobenzonitrile.

In another embodiment, (i) 2-cyanobenzenesulfonyl chloride is heated to a temperature of about 0° C. to about 100° C. with a first alkali metal fluoride in solvent for the 2-cyanobenzenesulfonyl chloride for a time sufficient to provide 2-cyanobenzenesulfonyl fluoride and (ii) the 2-cyanobenzenesulfonyl fluoride is heated in the presence of a second alkali metal fluoride under conditions and for a time sufficient to provide 2-fluorobenzonitrile; this embodiment is advantageous because the overall yield of 2-fluorobenzonitrile is higher.

Methods for converting sulfonyl chlorides to sulfonyl fluorides are known in the art. To practice present step (i), one skilled in the art may select any one of these known methods to convert 2-cyanobenzenesulfonyl chloride. For example, W. Davies et al., "286 - Aromatic Sulphonyl Fluorides. A Convenient Method of Preparation", *J. Chem. Soc.* 2104 (1932) teach a method which involves refluxing an aqueous solution of an alkali metal fluoride such as potassium fluoride, because of its high water solubility, with the sulfonyl chloride compound. This method is simple and inexpensive; the success of this method depends upon the faster conversion of the sulfonyl chloride group to the sulfonyl fluoride group relative to hydrolysis of the sulfonyl chloride. This method is not amenable to water sensitive compounds.

As another example, A. Sekiya et al., "Preparation of Aroyl and Arenesulfonyl Fluorides from the Corresponding Chlorides using Zinc Fluoride-Pyridine System", *Bull. Chem. Soc. Japan* 51(4). 1267 (1978) teach a method which uses anhydrous zinc fluoride in pyridine to effect the conversion. Although the yields are good, zinc fluoride is relatively expensive, pyridine has an unpleasant odor, and the workup is somewhat tedious.

As another example, D. Farney et al., "Sulfonyl Fluorides as Inhibitors of Esterases. I. Rates of Reaction with Acetylcholinesterase, alpha-Chymotrypsin, and Trypsin", *J. Am. Chem. Soc.* 85, 997 (1963) teach a method which involves heating sodium or potassium fluoride in an inert solvent such as sulfolane. Yields are moderate but the separation of the 2-cyanobenzenesulfonyl fluoride from the solvent may be difficult.

As another example, T. Bianchi et al., "Phase Transfer Catalysis. Preparation of Aliphatic and Aromatic Sulfonyl Fluorides", *J. Org. Chem.* 42, 2031 (1977) teach a method which involves reacting the sulfonyl chloride with alkali metal fluoride such as potassium fluoride in solvent for the aromatic sulfonyl chloride such as acetonitrile and having a phase transfer catalyst such as crown ether therein at room temperature. This method is preferred for the conversion of 2-cyanobenzenesulfonyl chloride to 2-cyanobenzenesulfonyl fluoride because the yields are excellent, the workup is simple, and the solvent is easily recovered. For the present invention, the mixture may be heated to a temperature of about 0° C. to about 100° C. Preferably, the mixture is heated to a temperature of about 25° C. to about 80° C., and more preferably, about 35° C. to about 40° C.

In part (ii), the 2-cyanobenzenesulfonyl fluoride is heated in the presence of a second alkali metal fluoride under conditions and for a time sufficient to provide 2-fluorobenzonitrile. Preferably, the mixture is heated to a temperature of about 180° C. to about 280° C., more preferably about 230° C. to about 260° C., and most preferably about 240° C. to about 255° C.

The second alkali metal fluoride is an alkali metal fluoride selected from the group consisting of sodium fluoride, potassium fluoride, rubidium fluoride, and cesium fluoride. Commercially available sodium fluoride, potassium fluoride, rubidium fluoride, and cesium fluoride may be used in the present invention. The preferred alkali metal fluoride is potassium fluoride which has been spray-dried so as to provide finely divided particles.

The molar ratio of 2-cyanobenzenesulfonyl fluoride to the second alkali metal fluoride is preferably about 0.4:1 to about 1:3. More preferably, the molar ratio is about 0.8:1 to about 1:2, and most preferably, the molar ratio is about 1:1 to about 1:2.

The 2-cyanobenzenesulfonyl fluoride and second alkali metal fluoride are heated to a temperature sufficient to initiate the reaction; evidence of reaction initiation is the evolution of sulfur dioxide. Although the reaction will proceed in the absence of a solvent, it is preferred to heat the 2-cyanobenzenesulfonyl fluoride and second alkali metal fluoride in a solvent. Any inert polar organic solvent may be used. Preferred solvents are amide solvents such as dimethylformamide, N-methylpyrrolidinone, sulfoxide solvents such as dimethylsulfoxide, and sulfone solvents. Most of these solvents are available in commercial quantities. Sulfone solvents are more preferred because they are most inert toward the reactions under the operating conditions of the present process.

Of the sulfone solvents, the most preferred are aliphatic sulfones of the formula: $R_1-SO_2-R_2$ where $R_1$ and $R_2$ are the same or different and are alkyl groups of generally about 1 to about 8 carbon atoms, and preferably, about 1 to about 4 carbon atoms or $R_1$ and $R_2$ together are alkylene units of about 4 to about 5 carbon atoms. Illustrative aliphatic sulfone solvents include dimethylsulfone, diethylsulfone, dipropylsulfone, dibutylsulfone, dipentylsulfone, dihexylsulfone, diheptylsulfone, dioctylsulfone, methylethylsulfone, tetramethylenesulfone, and pentamethylenesulfone. The most preferred aliphatic sulfone solvent is tetramethylenesulfone. Most of the aliphatic sulfone solvents are available in commercial quantities; otherwise, the compounds may be prepared by oxidation of the appropriate alkyl sulfide.

The purpose of the solvent is to dissolve the 2-cyanobenzenesulfonyl fluoride so as to form a stirrable mixture. Thus, as those skilled in the art will appreciate, the amount of solvent needed will depend upon the particular solvent selected.

If a solvent is not employed, a phase transfer catalyst may be used. Useful phase transfer catalysts include 18-crown-6, dibenzo-18-crown-6, and quaternary ammonium salts which are stable at the reaction temperature.

The time required for reaction depends upon the temperature used. Typically, the time for converting 2-cyanobenzenesulfonyl fluoride to 2-fluorobenzonitrile is about one to about four hours. The reaction is conveniently monitored by the evolution of the sulfur dioxide gas.

The 2-fluorobenzonitrile is isolated from the reaction mixture by a known technique such as distillation. The preferred isolation technique is distillation because it permits the solvent to be recycled without any need for additional purification.

As mentioned earlier, 2-fluorobenzonitrile is a versatile intermediate for a variety of 2-fluoro substituted benzenes. For example, hydrolysis of 2-fluorobenzonitrile leads to 2-fluorobenzoic acid or 2-fluorobenzamide while reduction of 2-fluorobenzonitrile leads to 2-fluorobenzylamine. Also, the reaction of 2-fluorobenzonitrile with organometallic reagents results in various 2-fluorophenyl ketones.

The present invention is more fully illustrated by the following non-limiting Examples.

EXAMPLE 1

This Example is directed to the preparation of 2-cyanobenzenesulfonyl chloride.

44 grams(0.24 mole) of saccharin and 100 grams(0.48 mole) of phosphorus pentachloride were stirred at 110° C. to 120° C. for 3.5 hours. The reaction mixture was then poured into 500 milliliters of ice and water, stirred until solidified, filtered, ground with water, re-filtered, and dried to give 44.3 grams of 2-cyanobenzenesulfonyl chloride and pseudosaccharin chloride. Based on saccharin, the per cent yield was 92.

EXAMPLE 2

This Example is directed to the preparation of 2-cyanobenzenesulfonyl fluoride by using the product of Example 1.

A mixture of 37.2 grams(0.18 mole) of the product prepared in Example 1, 200 milliliters acetonitrile, 25 grams(0.43 mole) spray-dried potassium fluoride, and 0.3 gram dibenzo-18-crown-6 was stirred at room temperature for four hours. The mixture was filtered and volatiles were removed by rotary evaporation. The residue was taken up in methylene chloride and filtered; after removal of the methylene chloride, 27.3 grams of solid remained. Recrystallization from 50 milliliters 75% ethanol/water gave 24.7 grams white solid 2-cyanobenzenesulfonyl fluoride having a melting point of 88°–90° C. Based on 2-cyanobenzenesulfonyl chloride, the per cent yield of 2-cyanobenzenesulfonyl fluoride was 77. Based on saccharin, the overall yield was 71.

EXAMPLE 3

This Example is directed to the preparation of 2-fluorobenzonitrile in solvent by using the product of Example 2.

15 milliliters sulfolane, 3.2 grams(0.055 mole) spray-dried potassium fluoride, and 10.2 grams(0.055 mole) of the 2-cyanobenzenesulfonyl fluoride prepared in Example 2 above were heated under nitrogen at 250° C. for one hour. The product was distilled directly from the resultant reaction mixture; the product weighed 5.6 grams and was identified by infrared spectroscopy as 2-fluorobenzonitrile. Based on 2-cyanobenzenesulfonyl fluoride, the per cent yield of 2-fluorobenzonitrile was 84. Based on saccharin, the overall yield was 60.

EXAMPLE 4

This Example is directed to the preparation of 2-fluorobenzonitrile in the absence of solvent by using the product of Example 2.

A mixture of 3.2 grams(0.055 mole) potassium fluoride, 10.2 grams(0.055 mole) of 2-cyanobenzenesulfonyl fluoride prepared in Example 2 above, and 0.1 gram dibenzo-18-crown-6 was stirred and heated under nitrogen at 225°–245° C. for two hours. The product was then vacuum distilled from the reaction mixture and weighed 2.9 grams. Based on 2-cyanobenzenesulfonyl fluoride, the per cent yield of 2-fluorobenzonitrile was 44. Based on saccharin, the overall yield was 31.

EXAMPLE 5

This Example is directed to the preparation of 2-fluorobenzonitrile by using the product of Example 1.

20.15 grams(0.1 mole) of the product prepared in Example 1 above, 12 grams(0.21 mole) spray-dried potassium fluoride, and 45 milliliters sulfolane were heated under nitrogen to 230°-248° C. for one hour. The product was distilled directly through a 5-inch(12.7 centimeters) vigreaux column to give 6.9 grams 2-fluorobenzonitrile having a boiling point of 91°-92° C. at 27 mm Hg. The infrared spectrum was identical with that of the published spectrum. Based on 2-cyanobenzenesulfonyl chloride, the per cent yield of 2-fluorobenzonitrile was 57. Based on saccharin, the overall yield was 52.

Having described the invention in detail and by reference to preferred embodiments thereof, it will be apparent that modifications and variations are possible without departing from the scope of the invention defined in the appended claims.

What is claimed is:

1. A process for the preparation of 2-fluorobenzonitrile comprising the steps of:
   (a) heating 2-cyanobenzenesulfonyl chloride with alkali metal fluoride in solvent for said 2-cyanobenzenesulfonyl chloride to a temperature of about 170° C. to about 250° C. for a time sufficient to provide 2-fluorobenzonitrile; and
   (B) isolating said 2-fluorobenzonitrile from said reaction mixture.

2. The process of claim 1 wherein said mixture is heated to a temperature of about 210° C. to about 245° C.

3. The process of claim 1 wherein said mixture is heated to a temperature of about 225° C. to about 235° C.

4. The process of claim 1 wherein said alkali metal fluoride is an alkali metal fluoride selected from the group consisting of sodium fluoride, potassium fluoride, rubidium fluoride, and cesium fluoride.

5. The process of claim 1 wherein said alkali metal fluoride is potassium fluoride.

6. The process of claim 1 wherein said solvent is selected from the group consisting of tetramethylenesulfone, dimethylsulfone, diethylsulfone, dipropylsulfone, dibutylsulfone, dipentylsulfone, dihexylsulfone, diheptylsulfone, dioctylsulfone, methylethylsulfone, and pentamethylenesulfone.

7. The process of claim 1 wherein said solvent is tetramethylenesulfone.

8. A process for the preparation of 2-fluorobenzonitrile comprising the steps of:
   (a) heating saccharin and phosphorus pentachloride under conditions and for a time sufficient to provide a mixture of 2-cyanobenzenesulfonyl chloride and pseudosaccharin chloride;
   (b) reacting said mixture of 2-cyanobenzenesulfonyl chloride and pseudosaccharin chloride with alkali metal fluoride in solvent for said 2-cyanobenzenesulfonyl chloride under conditions and for a time sufficient to provide 2-fluorobenzonitrile; and
   (c) isolating said 2-fluorobenzonitrile from said reaction mixture.

9. The process of claim 8 wherein in said step (a), said saccharin and phosphorus pentachloride are heated to a temperature of about 50° C. to about 150° C.

10. The process of claim 8 wherein in said step (b), said mixture is heated to a temperature of about 170° C. to about 250° C.

11. The process of claim 10 wherein in said step (b), said mixture is heated to a temperature of about 210° C. to about 245° C.

12. The process of claim 10 wherein in said step (b), said mixture is heated to a temperature of about 225° C. to about 235° C.

13. The process of claim 10 wherein said alkali metal fluoride is an alkali metal fluoride selected from the group consisting of sodium fluoride, potassium fluoride, rubidium fluoride, and cesium fluoride.

14. The process of claim 10 wherein said alkali metal fluoride is potassium fluoride 15. The process of claim 10 wherein said solvent is selected from the group consisting of tetramethylenesulfone, dimethylsulfone, diethylsulfone, dipropylsulfone, dibutylsulfone, dipentylsulfone, dihexylsulfone, diheptylsulfone, dioctylsulfone, methylethylsulfone, and pentamethylenesulfone.

16. The process of claim 10 wherein said solvent is tetramethylenesulfone.

17. The process of claim 8 wherein said step (b) comprises the steps of:
   (i) heating said 2-cyanobenzenesulfonyl chloride to a temperature of about 0° C. to about 100° C. with a first alkali metal fluoride in said solvent for a time sufficient to provide 2-cyanobenzenesulfonyl fluoride; and
   (ii) heating said 2-cyanobenzenesulfonyl fluoride in the presence of a second alkali metal fluoride under conditions and for a time sufficient to provide said 2-fluorobenzonitrile.

18. The process of claim 17 wherein in said step (ii), said 2-cyanobenzenesulfonyl fluoride is heated to a temperature of about 180° C. to about 280° C.

19. The process of claim 17 wherein in said step (ii), said second alkali metal fluoride is an alkali metal fluoride selected from the group consisting of sodium fluoride, potassium fluoride, rubidium fluoride, and cesium fluoride.

20. The process of claim 17 wherein in said step (ii), said second alkali metal fluoride is potassium fluoride.

* * * * *